United States Patent [19]

Chen

[11] Patent Number: 4,930,502
[45] Date of Patent: Jun. 5, 1990

[54] ANASTOMOSIS DEVICE

[76] Inventor: Fusen H. Chen, 240 Thompson Rd., Webster, Mass. 01570

[21] Appl. No.: 303,326

[22] Filed: Jan. 26, 1989

[51] Int. Cl.$^5$ ............................................. A61B 17/04
[52] U.S. Cl. ..................................................... 606/150
[58] Field of Search ............................ 128/334 C, 335

[56] References Cited

U.S. PATENT DOCUMENTS

| | | | |
|---|---|---|---|
| 2,453,056 | 11/1948 | Zack | 128/334 |
| 2,638,901 | 11/1953 | Sugarbaker | 128/334 C |
| 3,155,095 | 11/1964 | Brown | 128/334 |
| 3,254,650 | 6/1966 | Collito | 128/334 |
| 4,233,981 | 11/1980 | Schomacher | 128/334 R |
| 4,294,255 | 10/1981 | Geroc | 128/334 C |
| 4,523,592 | 6/1985 | Daniel | 128/334 C |
| 4,624,255 | 11/1986 | Schenck, et al. | 128/334 R |
| 4,657,019 | 4/1987 | Walsh, et al. | 128/334 C |
| 4,693,249 | 9/1987 | Schneck, et al. | 128/334 R |
| 4,705,039 | 11/1987 | Sakaguchi, et al. | 128/334 C |
| 4,728,328 | 3/1988 | Hughes, et al. | 623/12 |
| 4,747,407 | 5/1988 | Liu, et al. | 128/334 C |

Primary Examiner—Edward M. Coven
Assistant Examiner—Gary Jackson
Attorney, Agent, or Firm—Morris Kaplan

[57] ABSTRACT

An anastomosis device for interconnecting the ends of two tubular organs has, in a preferred embodiment, two circular members, each member having an outer region engagable against the contact surface of the outer region of the other member. When so engaged, both members are concentrically disposed about a common axis. Both members also have an inner region disposed concentrically within the outer region and including a concentric opening for receiving the end of a tubular organ. Both members also have a series of pins mounted in the inner region, disposed around the periphery of the opening and nearly parallel to the common axis so that the exposed ends of the pins approximately define a plane, for holding the ends of the tubular organ inserted into concentric opening.

20 Claims, 8 Drawing Sheets

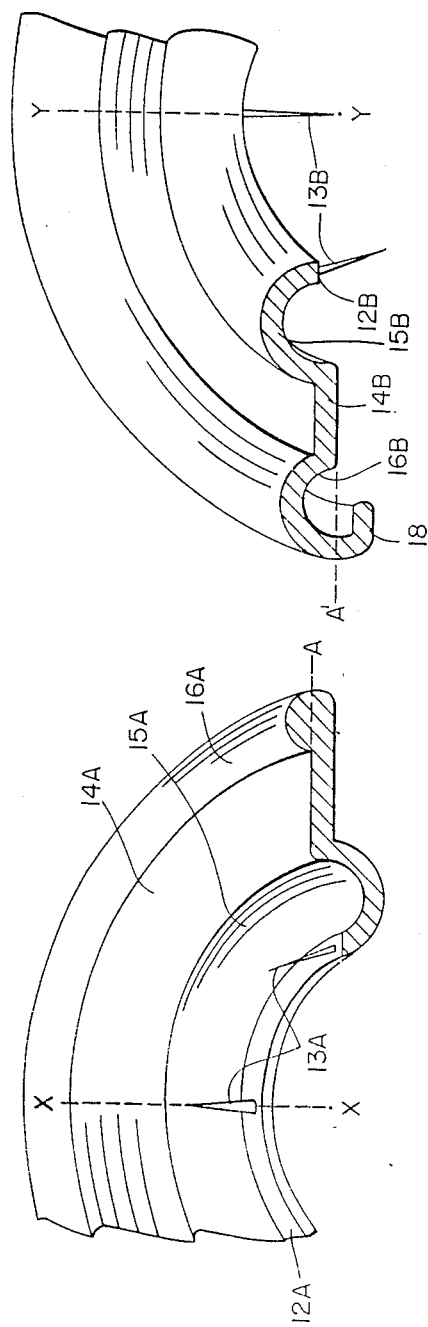

ANASTOMOSIS DEVICE

TECHNICAL FIELD

The invention relates to the field of surgery, more specifically to the anastomosis of luminal structures in the human body.

BACKGROUND OF INVENTION

A variety of devices are known in the prior art for performing anastomosis of luminal structures in the human body. The following disclosures are typical. U.S. Pat. No. 3,254,650 discloses a pair of tubes having ring-shaped flanges at one end thereof which are disposed around each end of the tubular organ to be anastomosed and are secured together by a retaining ring (see FIG. 5 thereof) that clamps over the flanges. The tissue can also be everted over the inner face of each of the annular flanges so that the two flanges are secured together by a plurality of pins which pierce the everted tissue and are secured in apertures disposed in the opposing flange member (see particularly FIGS. 20 and 21).

U.S. Pat. No. 4,523,592 discloses a pair of coupling disc members which cooperate to couple tubular structures of the body, such as bile ducts and blood vessels. One of the members has spaced apart hook members and the other member has receptive cavities aligned with the hook members for locking the members together in a anastomosis procedure with tissue everted and secured on the hook members.

U.S. Pat. No. 4,233,981 discloses a pair of annular flanges each formed of a plastic material for closing severed body vessels. Pointed pins on one of the flanges are pierced through the vessel walls and inserted into apertures in the other flange to hold and locate the vessel walls. Threaded nuts are threaded onto threaded pins to clamp the vessel walls together with a clamping pressure. The reference discloses that the inside diameter of the rings may be as small as four millimeters. The device is designed in such a way that the pressure exerted by the flange portions (rings) may be selected so that the connection is sufficiently tight to prevent leakage while at the same time connection may be loosened or released so as to prevent the vascular wall from becoming necrotic.

U.S. Pat. No. 3,155,095 discloses an absorbable anastomosis assembly comprising a hollow cylinder which is inserted into each end of a pair of vascular vessels to be anastomosed such that the ends of the vessels are in an abutting relation. An external cylindrical sleeve fits over the outer surface of the positioned vessels to be anastomosed and is clamped over the abutting end portions of the vascular vessels. The hollow cylinder and the sleeve are made of an absorbable material, such as reconstituted collagen or oxidized cellulose, so that the material is absorbed by the body slowly over time until epithelization occurs.

U.S. Pat. No. 4,294,255 discloses a pair of ring shaped members which are disposed interluminally in the tubular organ to be anastomosed. The confronting faces of the device have an annular, sharpened rim located at a radially innermost position. Tissue from the organ to be anastomosed is positioned between the confronting faces of the rings and the rings are secured by tooth pins that are retained in openings in the ring to securely clamp the rings and the intervening tissue together.

U.S. Pat. No. 2,453,056 discloses an anastomosis apparatus in which a tube having a flange at one end thereof and grooves in the outer surface of the tube, is placed over one of the tubular organs to be anastomosed. The tissue of the tubular organ is then everted over the outer surface of the tube and the other end of the tubular structure organ to be anastomosed is pulled over the everted surface of the first tubular organ. A pair of rings are slid over the two ends of the tubular organ to be anastomosed and are held in position by the grooves in the outer surface of the anastomosis tube. In this manner the intima of the tubular organs to be anastomosed are positioned facing each other. The reference also discloses an anastomosis device comprising a tube having a flange disposed at one end thereof which is slid over one end of the tubular organ to be anastomosed and the tissue of the end is everted over the outer surface of the tube. A ring shaped spring clamp is slid over the other end of the tubular organ to be anastomosed and the other end is positioned over the everted tissue held in position by the outer surface of the tube such that the ring shaped spring clamp clamps over the tube with the two tubular organs sandwiched therebetween.

U.S. Pat. No. 4,693,249 discloses a ring shaped anastomosis device having outer surface protrusions for impaling a pair of living vessel ends thereon without any sutures. A first vessel end is inserted through a central opening of the device, everted around the end of the device and impaled on the protrusion; then a second end vessel is drawn over the everted first vessel and similarly impaled on the protrusions.

U.S. Pat. No. 4,624,255 discloses a suturing ring which is structured for suturing the blood vessel portions thereto under radial stress with the intima of the blood vessel portions apposed. U.S. Pat. No. 4,705,039 discloses a subsidiary device for suturing an intestine. The tubes are disposed in the interior lumina of the intestine to be anastomosed such that the male tube is adapted to fit into a female tube which are then secured together by a pin. U.S. Pat. No. 4,728,328 discloses a cuff tubular organic prosthesis.

U.S. Pat. No. 4,705,039 discloses a subsidiary device for suturing an intestine. The tubes are disposed in the interior lumina of the intestine to be anastomosed such that the male tube is adapted to fit into a female tube which are then secured together by a pin.

U.S. Pat. No. 4,728,328 discloses a cuff tubular organic prosthesis.

A typical problem with prior art anastomosis devices is that they have no ready means for keeping the forces to which the tubular organs are subjected within controlled limits, causing interruption of the blood supply, among other things, with the result that their tissue may experience only slow healing or even necrosis.

SUMMARY OF THE INVENTION

The present invention does not generally require everting or sandwiching of the tissue and this avoid interruption of the blood supply and necrosis. The invention utilizes a structure having a series of pins disposed around the periphery of each tubular organ to hold the organs in fixed relation to one another. In preferred embodiments, pins from one part of the structure enter extraluminally into a first one of the tubular organs but then extend, almost parallel to the luminal axis, into the wall of the second tubular organ; and similarly, pins from a different part of the structure enter extraluminally into the second tubular organ but then extend, almost parallel to the luminal axis, into the wall of the first tubular organ. Pins from each part of the structure alternate around the luminal axis.

BRIEF DESCRIPTION OF THE DRAWINGS

FIGS. 2A and 2B show cut away views of a portion of the male and female annular members respectively of FIGS. 1A and 1B.

DETAILED DESCRIPTION OF THE DRAWINGS

The present invention provides for a human tubular organ anastomosis device, for uses including but not limited to, blood vessel anastomosis, including small blood vessel micro-anastomosis, as well as the anastomosis of intestines, vas deferens, billiary duct, urethra, ureter, etc. The device is meant to replace conventional sutures and metal staples.

Figure 1B:
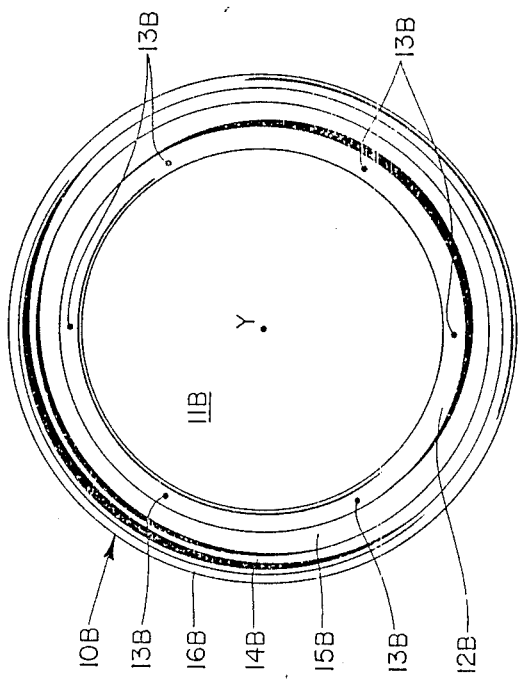
FIGS. 1A and 1B show inside plan views of male and female annular members respectively of an anastomosis device according to a preferred embodiment of the invention.
Figure 1A:
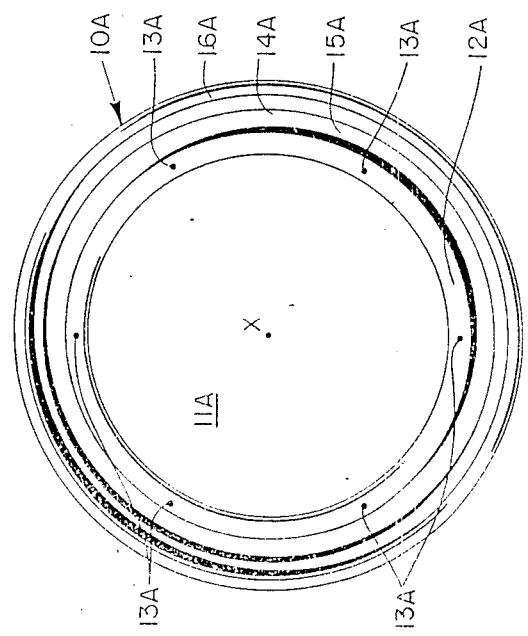

FIGS. 1A and 1B show plan views of the male 10A and the female 10B annular members of an anastomosis device according to a preferred embodiment of the invention. The annular members 10A and 10B have central axes, perpendicular to the page, X and Y respectively. In use of the device, one end of a first luminal tubular organ to be anastomosed is passed through opening 11A of the male member, while the end of a second tubular organ is similarly passed through opening 11B of the female member. The end of each organ is disposed to point upward from the page and its luminal axis is approximately coincident with the annular member's central axis. Lips 12A and 12B at the inner periphery of each member have a series of pins 13A and 13B respectively disposed around the periphery thereof, and disposed approximately parallel to the central axes X and Y respectively. In many cases it is preferable, as discussed below in connection with FIG. 4, that the pins in each series form a small angle, for example, approximately 15°, with the central axis, so that the exposed ends of the pins in each series lie at a slightly smaller radial distance from the central axis than do the bases of the pins. The radius of the interior hole in the members 10A and 10B is selected to correspond with the outer radius of the luminal members to be anastomosed. In this manner the exterior wall of the first tubular organ near its end is pierced and engaged by the series of pins 13A and the exterior wall of the second tubular organ near its end is pierced and engaged by the series of pins 13B. Generally the engagement may be achieved without substantial eversion of the tubular organ, and it can be seen that the series of pins associated with each annular member maintains the patency of its respectively held tubular organ. The outer regions of the male and female members include mating attachment elements 16A and 16B respectively in a manner described below, as well as 14A and 14B respectively, which are also described below.

FIGS. 2A and 2B show cut away views of the male and female members respectively of FIGS. 1A and 1B. Lip 12A and jaw 15A are shown in FIG. 2A, while lip 12B and jaw 15B are shown in FIG. 2B. In addition, FIG. 2A shows a projecting ridge 16A around the outer periphery of the male member, and FIG. 2B shows a corresponding channel 16B around the outer periphery of the female member designed to receive projecting ridge 16A, with which it mates. It will be seen that the male and female members of this embodiment each exhibit radial symmetry, permitting the mating of the members without a specific radial orientation, as long as they are coaxial and the pins 13 on each member do not collide with one another.

Also shown in FIGS. 2A and 2B are contact surfaces 14A and 14B respectively (shown on the upward side in FIG. 2A and on the downward side in FIG. 2B) that are in contact with one another when the attachment elements 16A and 16B are mated. The arrangement of these contact surfaces permits there to be maintained a gap between the lips 12A and 12B when the male and female members are mated, as described in further detail below in connection with FIG. 3. The surfaces are here shown as flat; other surfaces are possible, as long as the geometry is such that the surfaces are in contact with one another when the male and female members are mated. Similarly, the attachment elements 16A and 16B are shown as a ridge and channel respectively, although other mating configurations are within the scope of the invention. The embodiment shown contemplates the use of resilient male and female members and also includes a retaining protrusion 18 disposed peripherally at the entrance to the channel 16B on the female member, so that when the male member's ridge 16A is pushed past the protrusion 18 of the female member, there is a very slight deformation of the members, permitting them to snap together. The ridge 16A is then held in place in the channel 16B by the retaining protrusion 18. The members can thereafter be manually unsnapped, if desired, but the geometry and materials are such that the members otherwise remain mated in usual circumstances.

Figure 3:
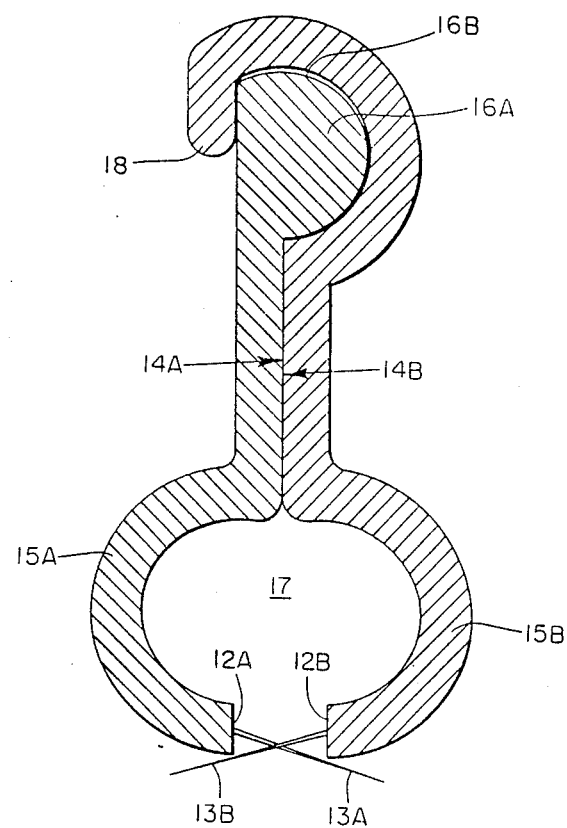
FIG. 3 shows a cross section taken through a radius of the mated male and female annular members of FIGS. 2A and FIG. 2B respectively.

FIG. 3 shows a cross section taken through a radius of the male and female members of FIGS. 2A and 2B respectively in mated position. Ridge 16A in the outer region of the male member is shown disposed within the channel 16B in the outer region of the female member. The ridge 16A and channel 16B are configured so that the contact surface 14A is engaged against contact surface 14B, and jaws 15A and 15B form space 17, when the male and female members are mated. The abutting contact surfaces 14A and 14B also maintain a gap between opposing lips 12A and 12B, from which protrude the pins 13A and 13B. It will be appreciated that the gap and the space 17 allow for inflammation and growth of the tissue secured to lips 12A and 12B.

Figure 4:
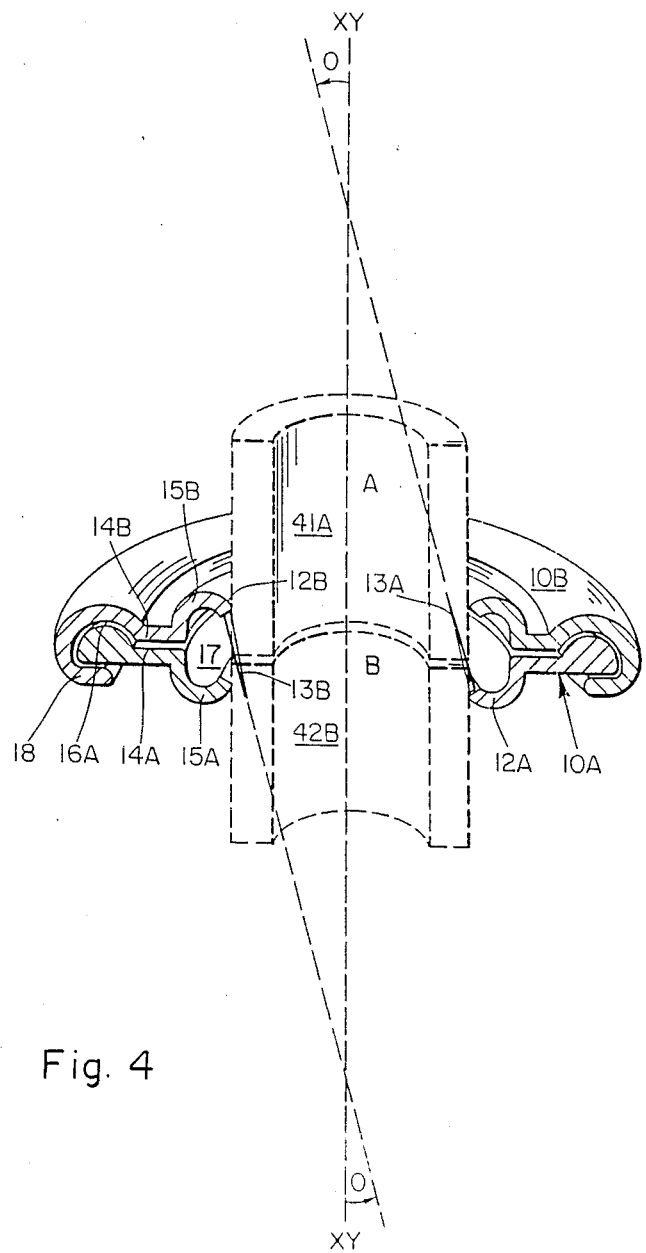
FIG. 4 shows a cut away view of the male and female members of FIGS. 1A and 1B as used in achieving anastomosis.

FIG. 4 shows the male and female members 10A and 10B respectively as used in achieving anastomosis. It will be seen that the central axes of X—X and Y—Y of the mated members 10A and 10B are coincident with each other and with the luminal axes of the tubular organs 41 and 42. This figure shows that the pins 13A of the male member 10A penetrate first the exterior wall of tubular organ 42 (to which it is first attached) but then extend (as a result of mating with the female member 10B) into the wall of tubular member 41. Similarly, the pins 13B of the female member 10B penetrate first the exterior wall of tubular organ 41 (to which it is first attached) but then extend (as a result of mating with male member 10A) into the wall of tubular member 42. Thus, following initial attachment of tubular organ 42 to male and member 10A and of tubular organ 41 to female member 10B in the manner described in connection with FIGS. 1A and 1B, the members are mated as described in connection with FIG. 3, and the tubular organs are held in relation to one another by virtue of attachment elements 16A and 16B described above; in addition, however, during the mating process, the pins 13A extending through the wall of organ 42 pierce the wall of organ 41 and the pins 13B extending through the wall of organ 41 pierce the wall of organ 42. The angle $\theta$ between the pins 13A and 13B and the central axes X—X, Y—Y is here somewhat exaggerated for purposes of illustration but is selected to facilitate penetration of the walls of the tubular members while avoiding undue or unnecessary penetration into the lumen and undue distortion of the tabular organ. It is typically preferable that the pins 13A and 13B alternate around the central axes. Mating can be achieved in such a way that spacing between successive pins from mating members is uniform, and, if desired, the member can be provided with a suitable keying arrangement to establish a desired relation of the two series of pins. It can be seen that no sandwiching of the organs is necessary using the present invention and that the forces present on the organs are relatively uniform around the entire anastomosed region, without interfering with the blood supply to the region. It can also be seen that the space 17 between the jaws 15A and 15B is available for inflammation and growth of the anastomosed tissue. Also, because the seal is relatively good between the exterior wall of the organs 41 and 42 and the lips 12A and 12B of the members 10A and 10B and because the seal between the members 10A and 10B is also good, the device minimizes leakage of fluid from the lumen.

Figure 5A:
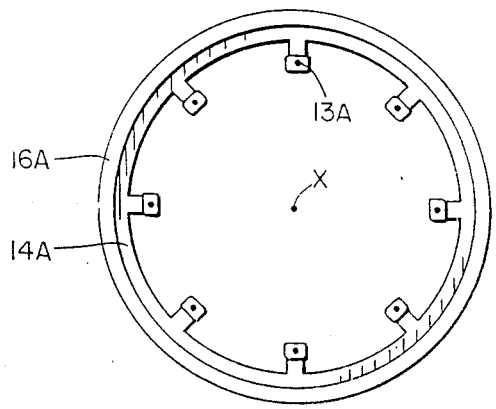
FIGS. 5A and 5B are plan and cutaway views of a male member of an alternative embodiment of the invention.
Figure 5B:
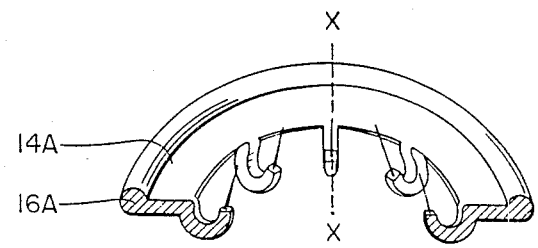

FIGS. 5A and 5B illustrate an alternative embodiment to that of the preceding figures. This embodiment is similar to the preceding embodiment, except that the mass of the annular member is reduced by eliminating material of the lips 12A and jaws 15A between each of the pins 13A, so that each pin 13A is mounted in relation to the outer region by means of a bridge 51. Although only the male plan and cut away views 5A and 5B (corresponding to FIGS. 1A and 1B respectively) are shown, the female member is similarly modified. In all other major respects this embodiment resembles that of the preceding figures.

Figure 5C:
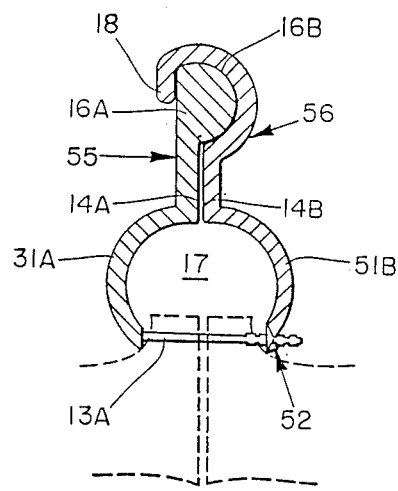
FIGS. 5C-5E show a variation of this embodiment.
Figure 5E:
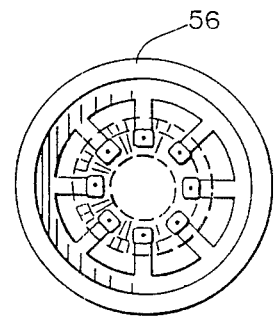
Figure 5D:
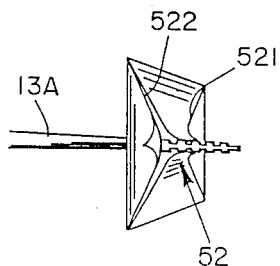

A variation of this embodiment is shown in FIG. 5C (which corresponds with FIG. 3 of the first described embodiment), wherein pins 13A emanate as before from bridge 51A of the male member 55 and not from the bridge 51B of the female member 56. In this embodiment however, alternate bridges of each member (for example shown here is the bridge 51B of the female member 56) are provided with an aperture 52 into which fits the pin from the mating member (for example here pin 13A from male member 55). As shown in FIG. 5D, each aperture 52 is formed by intersecting slits 522 and 521 so that material of the bridge at the boundary of the aperture has four pointed tips that are capable of gripping the inserted pin (13A). (The tip nearest the reader is shown bent away for clarity of the views.) The angles at which these tips grip the pin 13A can be oriented in a manner well known in the art of mechanical design, so that the force to remove the pin 13A from the aperture 52 is much greater than the force to insert the pin. In use of this embodiment the luminal organs to be anastomosed are partially everted to permit their being pierced by pins (13A). However, the relation between the bridges 51A and 51B and contact surfaces 14A and 14B is such that the forces on the tubular organs are prevented from being excessive. As can be seen FIG. 5E, in which is shown a top view of mated members 56 and 55 (with the luminal organ in cross section), the structure of bridges 51B and 51A is such that the anastomosed tissue need be only partially everted and there is ample space in which the anastomosed tissue may grow and heal.

Figure 6A:
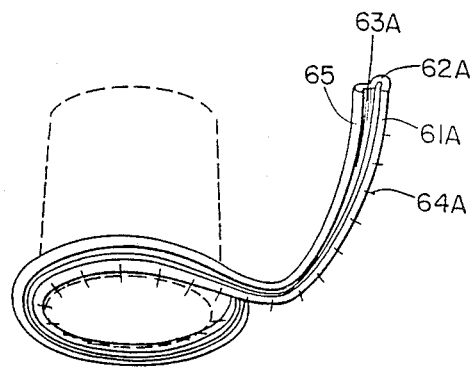
FIGS. 6A and 6B show male and female flexible strips respectively of an anastomosis device according to another preferred embodiment of the invention.
Figure 6B:
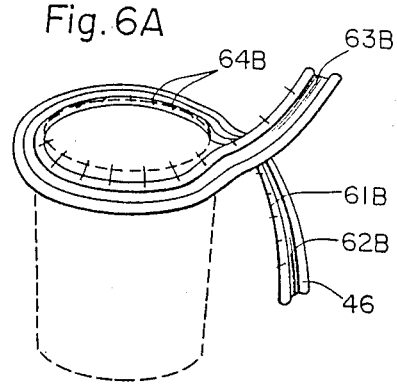
Figure 6C:
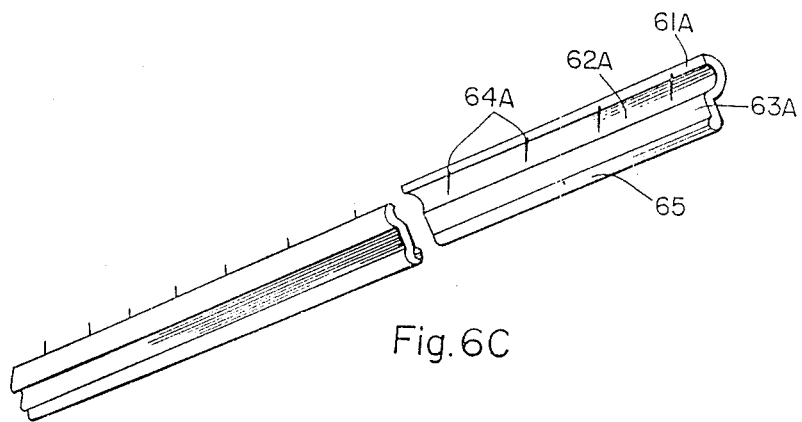
FIG. 6C shows a view of the flexible male and female strips respectively of FIGS. 6A and 6B as linearly disposed.

Another embodiment of the invention utilizes a pair of flexible strips in a manner analogous to the annular members described above. A male flexible strip is wrapped around the end of one of the tubular organs to be anastomosed as shown in FIG. 6A and a female flexible strip is wrapped around the end of the other of the tubular organs to be anastomosed as shown in FIG. 6B. The strips are held in place, prior to mating, with pins 64A and 64B. The strips are then mated in the general manner described above in connection with FIGS. 2, 3, and 4. The mated strips, uncurled and in a perspective cut away without tissue are shown in FIG. 6C. The male and female strips have respectively lips 61A and 61B, jaws 62A and 62B, contact surfaces 63A and 63B, and attachment elements 65 and 66 corresponding to similarly named items in the male and female annular members described above. The attachment element is a ridge 65 in the male and a channel 66 in the female. The channel includes a retaining protrusion as described above in connection with the annular members.

Figure 7A:
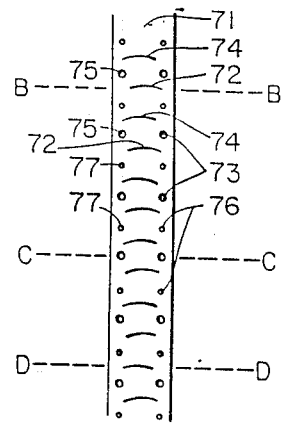
FIGS. 7A-7H illustrate another preferred embodiment of the invention, wherein the two main series of pins are carried on a single flexible strip.
Figure 7B:
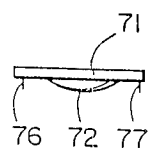
Figure 7C:
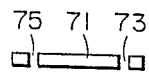
Figure 7D:
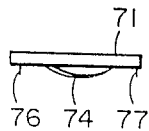
Figure 7E:
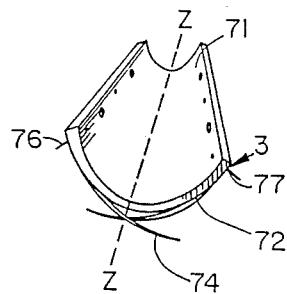
Figure 7F:
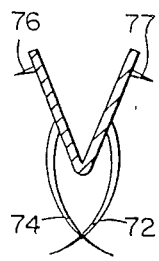
Figure 7G:
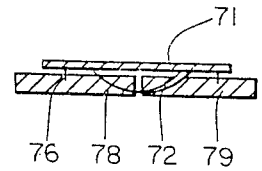
Figure 7H:
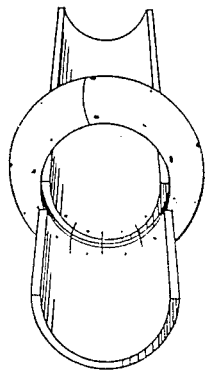

FIGS. 7A through 7H illustrate another embodiment of the invention in which a strip 71 of flexible material carries both the series of pins used to initially engage and hold a first tubular organ and the series of pins used to initially engage and hold a second tubular organ. As shown in FIG. 7A, a first series of pins 72 is mounted across the strip so that their bases are attached along the left edge of the strip and their exposed ends point toward the right edge of the strip. A second series of pins 74 is mounted across the strip on the same side of the stripped in the alternation with, the first series, oriented so that their bases are attached along the right edge of the strip and their exposed ends point toward the left edge of the strip. In alternation with each pin along the left edge is a short (e.g. about 2 mm) vertical pin 77, and in alternation with each pin along the right edge is a similar short vertical pin 76. FIGS. 7B through 7D are inverted horizontal cross sections taken through planes B—B, C—C and D—D respectively of FIG. 7A. It can be seen that the pins 72 and 74 are curved to facilitate engagement in the tubular organs and fastening of the pins in the manner described below. A series of buttom holes 75 and 78 appear along the left and right sides respectively of the strip in alternation with pins 77 and 76. In operation, as shown in FIG. 7E, the strip is first folded approximately along midline Z—Z into a shape the type illustrated in cross section in FIG. 7F. Then pins 74 are inserted around the end of a first tubular organ in the manner described above with respect to FIG. 6, and the pins 72 are inserted around the end of a second tubular organ. The strip 71 is also unfolded to produce anastomosis as shown in cross section FIG. 7G of the first organ 78 and the second organ 79. In the course of unfolding the strip, the exposed ends of the pins extend, from the walls of the organ into which they were initially inserted, into the walls of the other organ. The short pins 76 and 77 engage into the walls of tubular organs 78 and 79 respectively to prevent movement of the tubular organs with respect to the device or each other. In addition, one end of the strip 71 is linked by insertion of the pins 77 and 76 proximate thereto into the button holes 75 and 73 proximate to the other end of the strip, in such a way that the strip ends are tightly linked around the anastomosed organs. FIG. 7H shows a cut away view of the anastomosis device of this embodiment after anastomosis has been achieved.

It will be understood that the male and female members of each embodiment, including the pins, may be made of an absorbable material such as polyglycolic or polylactic compounds.

I claim:

1. An anastomosis device for interconnecting the ends of first and second tubular organs, the device comprising first and second members, each member including:
   (i) an outer region having a contact surface engagable against the contact surface of the other member and disposed about a central axis, the central axis of each of said members being coincident when the contact surfaces are engaged with one another;
   (ii) an inner region disposed concentrically within the outer region and including an opening located concentrically therein for receiving the end of said tubular organ; and
   (iii) a series of pins, each pin having a base, said pins being mounted at their bases in the inner region, disposed around the periphery of the opening and nearly parallel to the central axis so that the exposed ends thereof approximately define a plane, for holding said ends of said tubular organ inserted into said opening;
   so that anastomosis may be achieved.

2. A device according to claim 1, wherein each pin in the series of pins is so disposed as to form a small angle with the central axis in such a way that the exposed ends lie at a slightly smaller radial distance from the central axis than do the bases.

3. A device according to claim 2, wherein each pin is of such a length and is so located that the exposed ends associated with each member are capable of piercing not only tubular organ inserted through the hole of such member but also the tubular organ attached to the exposed ends associated with the other member.

4. A device according to claim 3, wherein the pins are so disposed that when the contact surfaces of the members are in engagement with one another there is formed a pattern around the coincident central axes in which pins from the first member alternate with pins from the second member.

5. A device according to claim 4, wherein the inner region of each member includes a lip on which are mounted the series of pins, the lip so disposed in relation to the outer region of such member that, when the contact surfaces of the members are in engagement with one another, there is defined between the lips a gap into which a portion of the tubular organs in the vicinity of the anastomosis may protrude.

6. A device according to claim 5, wherein each lip is affixed to a jaw, the jaw so disposed in relation to the outer region of such member that, when the contact surfaces of members are in engagement with one another, there is defined between the jaws a space to permit inflammation and growth of the anastomosed tissue therein so as to promote healing thereof.

7. A device according to claim 6, wherein the outer regions of the first and second members collectively include attachment means for attachment of one member to the other member.

8. A device according to claim 7, wherein the attachment means includes a projection from the outer region of the first member and a mating channel in the outer region of the second member, so that the projection is grabbed by the recess when the contact surfaces are engaged with one another.

9. A device according to claim 1, wherein each pin is of such a length and is so located that the exposed ends associated with each of said members are capable of piercing not only tubular organ inserted through the hole of such member but also the tubular organ attached to the exposed ends associated with the other member.

10. A device according to claim 9, wherein the pins are so disposed that when the contact surfaces of the members are in engagement with one another there is formed a pattern around the coincident central axes in which pins from the first member alternate with pins from the second member.

11. A device according to claim 10, wherein the inner region of each member includes a lip on which are mounted the series of pins, the lip so disposed in relation to the outer region of such member that, when the contact surfaces of the members are in engagement with one another, there is defined between the lips a gap into which a portion of the tubular organs in the vicinity of the anastomosis may protrude.

12. A device according to claim 11, wherein each lip is affixed to a jaw, the jaw so disposed in relation to the outer region of such member that, when the contact surfaces of members are in engagement with one another, there is defined between the jaws a space to permit inflammation and growth of the anastomosed tissue therein so as to promote healing thereof.

13. A device according to claim 10, wherein the outer region of the first and second members collectively include attachment means for attachment of one member to the other member.

14. A device according to claim 13, wherein the attachment means includes a projection from the outer region of the first member and a mating channel in the outer region of the second member, so that the projection is grabbed by the channel when the contact surfaces are engaged with one another.

15. A device according to claim 1, wherein the inner region of each member includes a lip on which are mounted the series of pins, the lip so disposed in relation to the outer region of such member that, when the contact surfaces of the members are in engagement with one another, there is defined between the lips a gap into which a portion of the tubular organs in the vicinity of the anastomosis may protrude.

16. A device according to claim 15, wherein each lip is affixed to a jaw, the jaw so disposed in relation to the outer region of such member that, when the contact surfaces of members are in engagement with one another, there is defined between the jaws a space to permit inflammation and growth of the anastomosed tissue therein so as to promote healing thereof.

17. A device according to claim 16, wherein the outer regions of the first and second members collectively include attachment means for attachment of one member to the other member.

18. A device according to claim 17, wherein the attachment means includes a projection from the outer region of the first member and a mating channel in the outer region of the second member, so that the projection is grabbed by the channel when the contact surfaces are engaged with one another.

19. A device according to claim 1, wherein the outer regions of the first and second members collectively include attachment means for attachment of one member to the other member.

20. A device according to claim 19, wherein the attachment means includes a projection from the outer region of the first member and a mating channel in the outer region of the second member, so that the projection is grabbed by the channel when the contact surfaces are engaged with one another.

* * * * *